(12) United States Patent
Kim et al.

(10) Patent No.: US 7,892,491 B2
(45) Date of Patent: Feb. 22, 2011

(54) APPARATUS FOR DISRUPTING CELLS OR VIRUSES USING LASER AND MAGNETIC BEADS

(75) Inventors: Su Hyeon Kim, Seoul (KR); Jeong Gun Lee, Seocho-gu (KR); Seung Yeon Yang, Seongnam-si (KR)

(73) Assignee: Samsung Electronics Co., Ltd. (KR)

( * ) Notice: Subject to any disclaimer, the term of this patent is extended or adjusted under 35 U.S.C. 154(b) by 778 days.

(21) Appl. No.: 11/533,961

(22) Filed: Sep. 21, 2006

(65) Prior Publication Data
US 2007/0071647 A1 Mar. 29, 2007

(30) Foreign Application Priority Data
Sep. 23, 2005 (KR) ...................... 10-2005-0088869

(51) Int. Cl.
*G01N 15/06* (2006.01)

(52) U.S. Cl. ...................... 422/68.1; 422/101; 422/102; 422/104; 435/287.2; 435/288.5; 435/288.7; 435/306.1

(58) Field of Classification Search .................. None
See application file for complete search history.

(56) References Cited

U.S. PATENT DOCUMENTS 6,255,118 B1 * 7/2001 Alfano et al. ............... 436/172
6,783,736 B1 * 8/2004 Taylor et al. ............... 422/103
6,815,209 B2 * 11/2004 Baeummer et al. ........... 436/63
2003/0096429 A1 5/2003 Baeumner et al.

OTHER PUBLICATIONS

Rapid Isolation of PCR-Ready DNA from Blood, Bone Marrow and Cultured Cells, Based on Paramagnetic Beads; Arne Deggerdal, Frank Larsen; BioTechniques 22:554-557 (Mar. 1997).
Rapid, Universal Method to Isolate PCR-Ready DNA Using Magnetic Beads; K. Rudi, M. Kroken, O.J. Dahlbert, A. Deggerdal, K.S. Jakobsen and F. Larsen; BioTechniques 22:5006-511 (Mar. 1997).
Lysing Bacterial Spores by Sonication through a Flexible Interface i a Microfluidic System; Michael T. Taylor, Phillip Belgrader, Burford J. Furman, Farzad Pouahmadi, Gregory T. A. Kovacs, and M. Allen Northrup; Anal. Chem. 2001, 73, 492-496.
Spatial Control of Cellular Measurements with the Laser Micropipet, Huaina Li, Christopher E. Sims, Hayley Y. Wu, and Nancy L. Allbritton; Anal. Chem. 2001, 73, 4625-4631.

* cited by examiner

Primary Examiner—Jill Warden
Assistant Examiner—Sally A Sakelaris
(74) Attorney, Agent, or Firm—Cantor Colburn LLP (57) ABSTRACT

An apparatus for disruption of cells or viruses using a laser and magnetic beads includes a cell lysis chip including a sample inlet hole into which a sample and the magnetic beads are introduced, a vibrator fixing the cell lysis chip and transferring vibrations in a prescribed direction, a laser generator supplying the laser to the cell lysis chip and a controller controlling operations of the vibrator and the laser generator.

15 Claims, 9 Drawing Sheets

APPARATUS FOR DISRUPTING CELLS OR VIRUSES USING LASER AND MAGNETIC BEADS

This application claims priority to Korean Patent application No. 2005-0088869 filed on Sep. 23, 2005, and all the benefits accruing therefrom under 35 U.S.C. §119, the contents of which are herein incorporated by reference in its entirety.

BACKGROUND OF THE INVENTION

1. Field of the Invention

The present invention generally relates to an apparatus for disruption of cells or viruses using a laser and magnetic beads, and more particularly, to an apparatus capable of effectively detecting DNA by rapidly disrupting cells or viruses using a laser and magnetic beads.

2. Description of the Related Art

Generally, a molecular diagnosis of a specific pathogenic microorganism is performed through the following four steps: 1) cell lysis, 2) DNA isolation, 3) DNA amplification and 4) DNA detection.

The DNA amplification includes a polymerase chain reaction ("PCR"), a ligase chain reaction, a stranded-displacement amplification, a nucleic acid-based amplification, a repair chain reaction, a helicase chain reaction, a Q beta ("QB") replicase amplification and a ligation activated transcription.

A method of isolating DNA from a cell is conducted with materials having a bonding affinity to DNA. Examples of the materials for DNA separation include silica, glass fiber, anion exchange resin and magnetic beads (see Rudi, K. et al., *Biotechniqures* 22, pp. 506-511, 1977 and Deggerdal, A. et al., *Biotechniqures* 22, pp. 554-557, 1997).

Cell lysis is conventionally performed by a mechanical, chemical, thermal, electrical, ultrasonic or microwave method (see Michael T. Talyer et al., *Anal. Chem.* 73, pp. 492-496, 2001).

The chemical method employs lytic agents for disrupting cells to release DNA. An additional treatment of cell extracts with a chaotropic reagent is necessary to denature proteins. The chemical lysis method is disadvantageous in that harsh chemicals are used to disrupt the cells. Since they can interfere with the subsequent PCR, it is necessary to purify the DNA prior to conducting the PCR. The chemical method is labor-intensive and time-consuming, requires expensive consumables and often has a low DNA yield. The thermal method involves repeated cycles of freezing/melting, but cannot often disrupt many structures within cells.

Heating is an alternative method of disrupting cell walls or membranes. One drawback of simple heating is that it causes the degeneration of proteins that can be attached to released DNA. They can also interfere with DNA amplification. A physical method employs a bulky and expensive pressure unit, but is not suitable for an LOC (Lab-on-a-Chip) application.

An ultrasonic treatment is an alternative of the physical method. In general, the ultrasonic treatment is performed in the state that a cell solution or suspension is put in a chamber located in an ultrasonic bath. However, such ultrasonic disruption has many disadvantages in terms of cell lysis. Firstly, a distribution of ultrasonic energy is not uniform. The non-uniform distribution of ultrasonic energy leads to inconsistent results. Secondly, due to the energy divergence in the ultrasonic bath, it often takes several minutes to completely disrupt cells. Lastly, the ultrasonic method generates unpleasant sounds.

A laser has a lot of advantages in view of the disruption of cells and can be readily applied to LOC (see Huaina Li, et al., *Anal. Chem.* 73, pp. 4625-4631, 2001). U.S. Patent Application Publication No. 2003/96429 A1 discloses a laser-induced cell lysis system. However, when only a laser is used, it is difficult to make an efficient cell lysis. As a result of doing an experiment using *E. coli* confirmed that low cell lysis efficiency is obtained when irradiated using a laser only. A concentration of DNA measured after irradiating a laser for 150 seconds is 3.77 ng/µl, whereas that of DNA measured after boiling cells at 95° C. for 5 minutes is 6.15 ng/µl. These results suggest that laser energy was not effectively transferred to cells Further, such conventional laser-induced cell lysis system has several problems in that it requires bulky and expensive units such as a laser generator and a converging lens, thereby increasing the production cost and making it unhandy to carry. In order to overcome the above problems, an attempt has been made to utilize a low-power laser generator. In such a case, however, there also exists a problem in that since a laser irradiation area is too small to fully cover a reaction area of cells or viruses to be subjected to cell lysis, a uniform and efficient cell lysis procedure cannot be performed.

BRIEF SUMMARY OF THE INVENTION

An exemplary embodiment provides a portable apparatus for disrupting cells or viruses using a laser and magnetic beads based on a cell lysis technique using an inexpensive laser diode.

An exemplary embodiment provides an apparatus for disruption of cells or viruses through the use of a holder structure which allows a cell lysis chip to vibrate substantially perpendicular to a laser irradiation direction and with a low-power laser without using any other diffusion lens, to thereby secure a wider laser irradiation area.

An exemplary embodiment provides an apparatus capable of rapidly and efficiently disrupting cells or viruses by using and vibrating both a laser and magnetic beads together.

An exemplary embodiment of an apparatus for disrupting cells or viruses using a laser and magnetic beads includes a cell lysis chip including a sample inlet hole into which a sample and the magnetic beads are introduced, a vibrator fixing the cell lysis chip and transferring vibrations in a prescribed direction, a laser generator supplying the laser to the cell lysis chip and a controller controlling operations of the vibrator and the laser generator.

In an exemplary embodiment, the vibrator includes a vibration motor, a holder including the vibration motor therein, fixing the cell lysis chip and transferring vibrations to the cell lysis chip, a shaft connecting the holder to the vibrator such that the holder is movable along with the vibrator and a restrictive member, such as a spring, inserted into the exterior of the shaft to elastically restricting the movement of the holder.

In an exemplary embodiment, the vibration motor may vibrate in a direction substantially perpendicular to a laser irradiation direction.

In an exemplary embodiment, the laser generator includes a laser diode ("LD") as a light source.

In an exemplary embodiment, the laser supplied by the laser diode has different vertical and horizontal irradiation angles.

In an exemplary embodiment, the laser generator includes a heat sink absorbing heat generated by the laser and dispersing the heat.

In an exemplary embodiment, the laser generator includes a temperature sensor detecting temperature calibration data of a temperature raised by laser irradiation and transmitting the detected temperature calibration data to the controller.

In an exemplary embodiment, the laser generator includes a cooling fan installed at one side of thereof, operated by the action of the controller and cooling down the heat generated within the apparatus by air.

In an exemplary embodiment, the cell lysis chip includes a chip body including a reaction chamber formed at the center thereof and an opened top surface, and a chip cover attached to the top surface of the chip body closing the upper portion of the reaction chamber, and allowing the laser to be passed through the reaction chamber, and having a sample inlet hole and a sample outlet hole formed to be penetrated towards the reaction chamber.

In an exemplary embodiment, the reaction chamber includes a reaction area wider than a laser irradiation area supplied by the laser generator.

In an exemplary embodiment, the controller includes a timer such that the laser diode and the driving motor are operated for a designated time period.

In an exemplary embodiment, the apparatus for disrupting cells or viruses further includes an auxiliary memory storing parameter data required for operation of the laser generator and transmitting the parameter data to the controller.

In an exemplary embodiment, the auxiliary memory may be one of EEPROM (Electrically Erasable Programmable Read Only Memory), UVEPROM (Ultra Violet Erasable PROM), flash memory and a combination including at least one of the foregoing.

In an exemplary embodiment, the apparatus for disrupting or viruses further includes a driving power source of the vibrator and the laser generator, the driving power source being a battery.

BRIEF DESCRIPTION OF DRAWINGS

The above and other objects and features of the instant invention will become apparent from the following description of preferred embodiments taken in conjunction with the accompanying drawings, in which.

DETAILED DESCRIPTION OF THE INVENTION

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. Like numbers refer to like elements throughout. As used herein, the term "and/or" includes any and all combinations of one or more of the associated listed items.

Spatially relative terms, such as "lower," "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, a preferred embodiment of the present invention will be descried in detail with reference to the accompanying drawings.

Figure 1A:
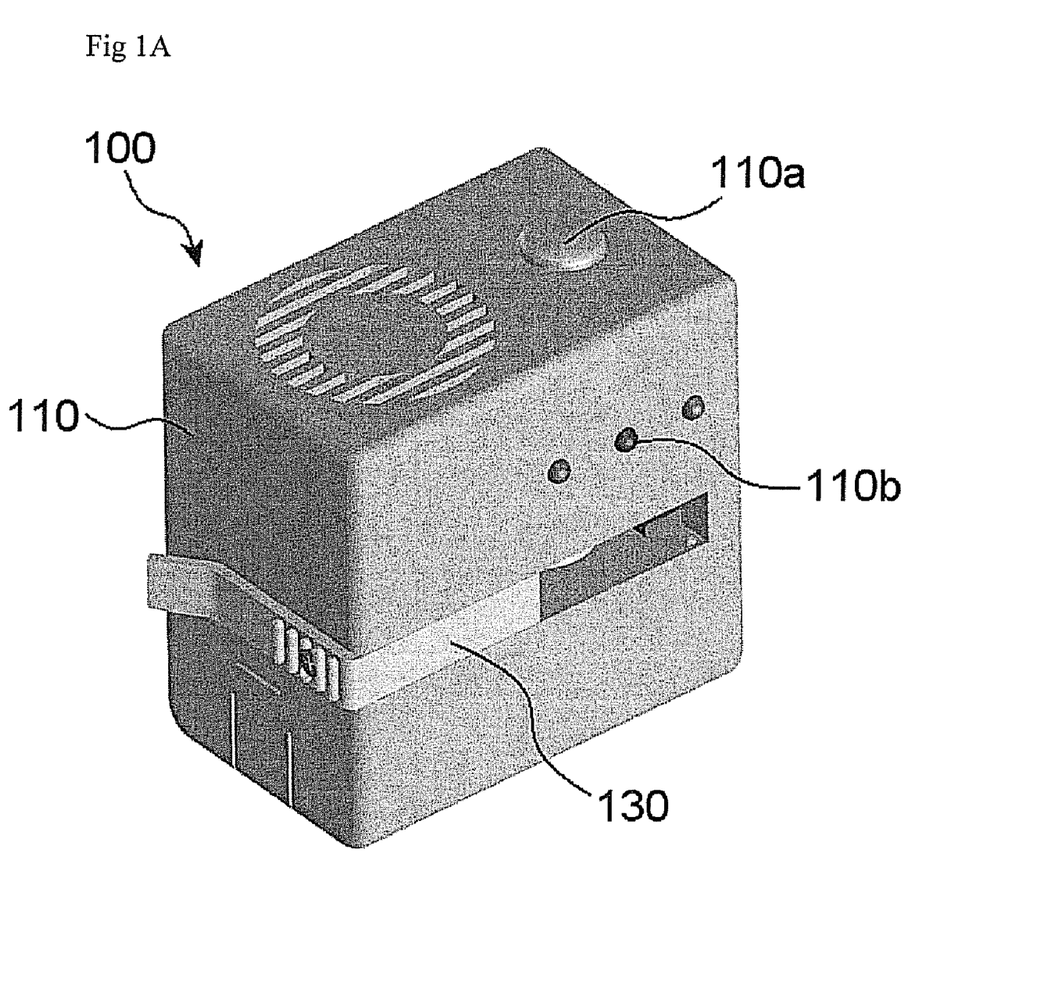
FIG. 1A is an exterior view of an exemplary embodiment of an apparatus for disrupting cells or viruses using a laser and magnetic beads according to the present invention.
Figure 1B:
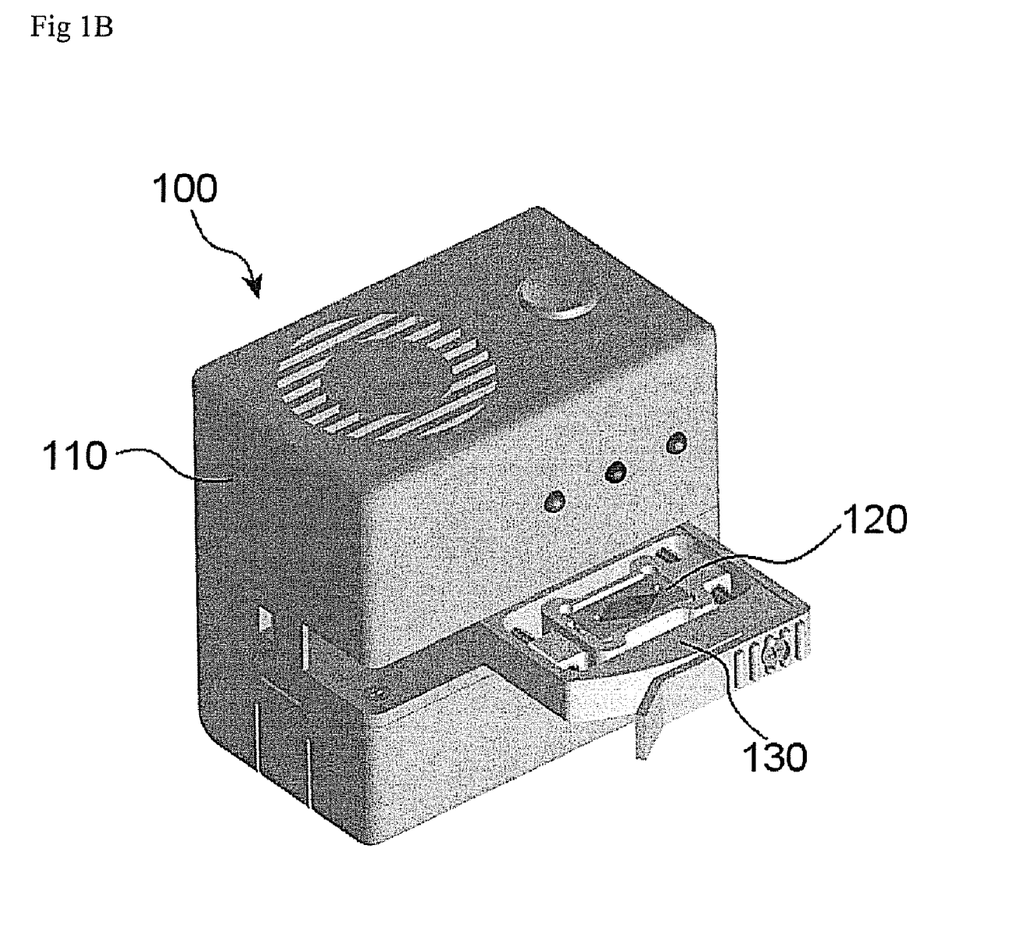
FIG. 1B is an exterior view thereof in a state that a vibrator is open.
Figure 2:
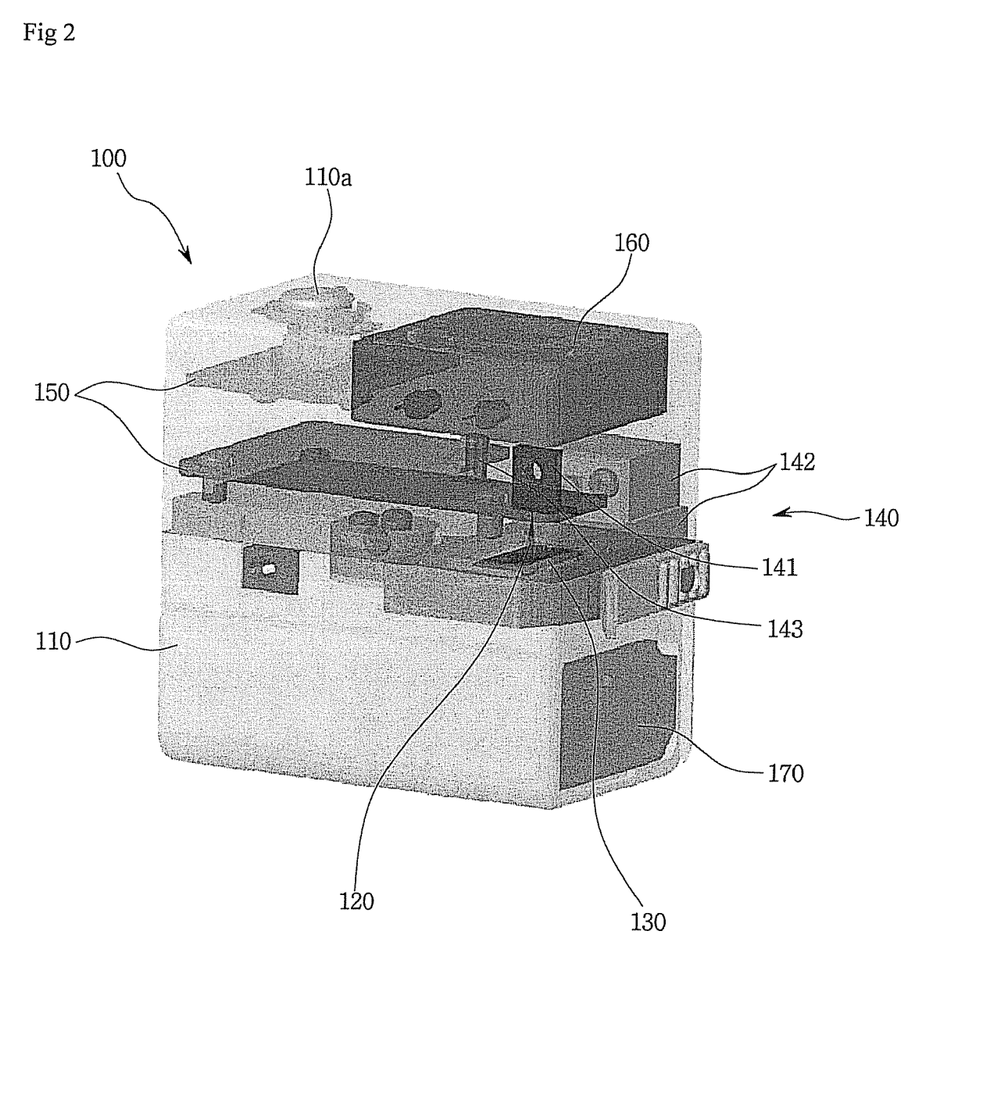
FIG. 2 is a perspective view illustrating an internal structure of the apparatus for disrupting cells or viruses using a laser and magnetic beads illustrated in FIG. 1A.

FIG. 1A is an exterior view of an exemplary embodiment of an apparatus for disrupting cells or viruses by using a laser and magnetic beads according to the present invention, and FIG. 1B is an exterior view thereof in a state that a vibrator is open. FIG. 2 is a perspective view illustrating an internal structure of the apparatus for disrupting cells or viruses by using a laser and magnetic beads described in FIG. 1A.

Referring to FIGS. 1A to 2, the apparatus 100 includes a cell lysis chip 120 into which a sample and magnetic beads are introduced, a vibrator 130—pivotally connected to a main body 110 and openable therefrom and functioning to fix the chip 120 and transfer vibrations in a prescribed direction, a laser generator 140 for supplying a laser to the chip 120 and a controller 150 controlling operations of the vibrator 130 and the laser generator 140.

The laser generator 140 is provided with a laser diode 141 used as a light source, a heat sink 142 that absorbs the heat generated by laser irradiation and disperses it, and a temperature sensor 143 installed at one side of the heat sink 142 for sensing the temperature raised by laser irradiation.

A cooling fan 160 may be installed at one side of the laser generator 140 for cooling down the heat generated within the apparatus, such as by circulating air. A power source 170 is built in at the lower portion of the vibrator 130 for supplying a power to and driving the apparatus. In an exemplary embodiment, the power source 170 may be in the form of a battery.

A switch 110a may be installed at the upper portion of the main body 110 and protrude from an upper surface of the main body 110 for the operation of the apparatus. A status identifier 110b, such as an LED lamp may be installed on the main body 110, such as illustrated at the front portion thereof in FIG. 1A, for displaying the operation status of the apparatus. In exemplary embodiments, the status identifier may include any of a number of features suitable for the purpose described herein, including but not limited to, digital or analog displays and/or audible signals.

As illustrated in the exemplary embodiment, the present invention can implement a self-operable and portable system for disrupting cells or viruses.

Figure 3A:
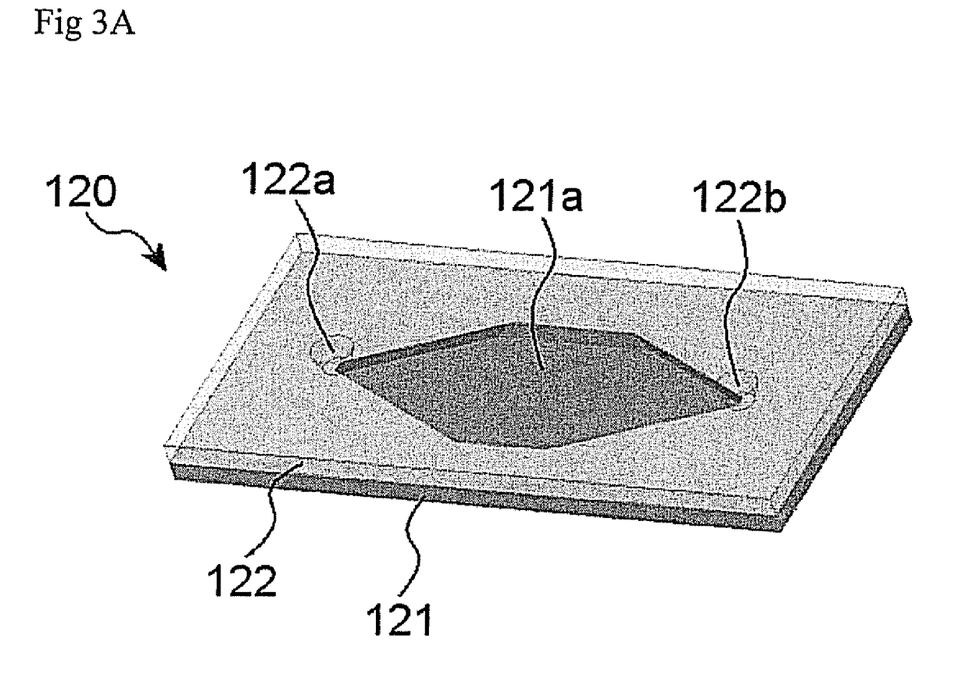
FIG. 3A is a perspective view illustrating an exemplary embodiment of a structure of a cell lysis chip according to the present invention.
Figure 3B:
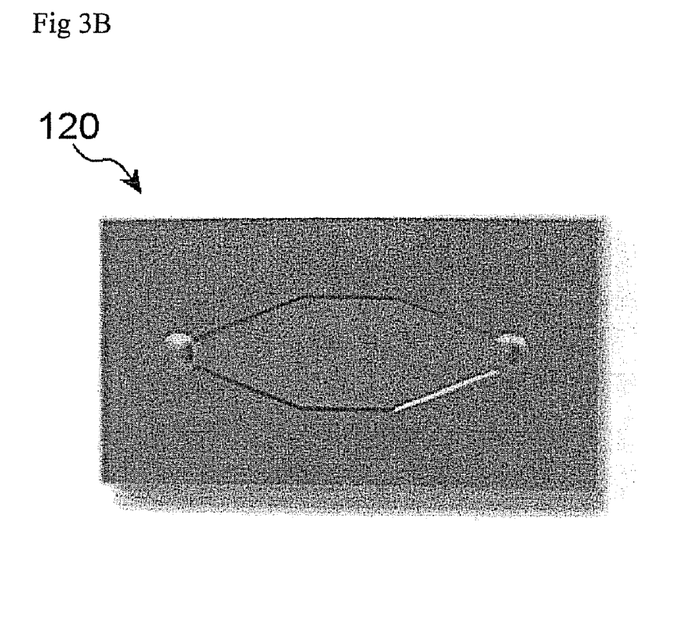
FIG. 3B is a photograph of the cell lysis chip.

FIG. 3A is a perspective view illustrating an exemplary embodiment of a structure of a cell lysis chip according to the present invention and FIG. 3B is a photograph of the cell lysis chip.

With reference to FIGS. 3A and 3B, the cell lysis chip 120 includes a chip body 121 having a reaction chamber 121a that may be formed substantially at the center thereof and have an opened top surface, and a chip cover 122 that is attached to the upper portion of the chip body 121 to close the upper portion of the reaction chamber 121a. The chip cover 122 may be formed to include a sample inlet hole 122a and an outlet hole 122b to be penetrated towards the reaction chamber 121a.

In an exemplary embodiment, the chip body 121 may be composed of glass, polymers and/or silicon. In one exemplary embodiment, the chip body 121 may be made by using a silicon wafer that can withstand a temperature of 100° C. or higher. An inner surface of the chip body 121 may be hydrophobically treated in order to prevent bubble generation by the reaction chamber 121a.

The chip cover 122 is attached to the top surface of the chip body 121 to close the upper portion of the reaction chamber 121a. The chip cover 122 is configured to permit the sample inlet hole 122a and the outlet hole 122b to be penetrated towards the reaction chamber 121a. In exemplary embodiments, the chip cover 122 may be made of materials having a transmittance of 90% or more in order to pass a laser through and within the chip. The chip cover 122 may be composed of glass, polymers, indium tin oxide ("ITO") glass and the like. In one exemplary embodiment, the chip cover 122 may be made of Pyrex 7740 glass. Alternatively, the chip cover 122 may be subjected to and include an anti-reflection ("AR") coating to increase the transmittance of the laser.

A mixture of a sample and magnetic beads (not shown) is introduced into the cell lysis chip 120 having a configuration such as in the illustrated exemplary embodiment, through the sample inlet hole 122a.

The magnetic beads absorb the laser beam and transfer heat and kinetic energy to cells. The magnetic beads heated by laser irradiation raise the temperature of a solution indirectly and disrupt the cell surface while contacting with cells directly.

In an exemplary embodiment, a diameter of the magnetic beads ranges from 50 nanometers (nm) to about 1,000 micrometers (μm). In one exemplary embodiment the diameter of the magnetic beads ranges from about 1 μm to about 50 μm. When the diameter of the magnetic beads is less than 50 nm, physical and mechanical shocks may be insufficient to cause cell lysis. When the diameter of the magnetic beads is greater than 1,000 μm, it may not be suitable for a lab-on-a-chip.

In exemplary embodiments, the magnetic beads may be any of a number of materials and magnetized. In one exemplary embodiment, the magnetic beads include at least one material selected from a group including, but not limited to, ferromagnetic Fe, Ni and Cr and oxides thereof. A surface of the magnetic beads can be formed to have polymers, organic materials, silicon and/or glass coated with a ferromagnetic metal. In exemplary embodiments, the surface of the magnetic bead has a negatively charged structure to which DNA is not attached in order to facilitate DNA purification procedures.

In an exemplary embodiment of a DNA purification procedure, the cell lysis chip 120 is fixed by the vibrator 130 and receives vibrations in a direction substantially perpendicular to a laser irradiation direction therefrom.

Figure 4:
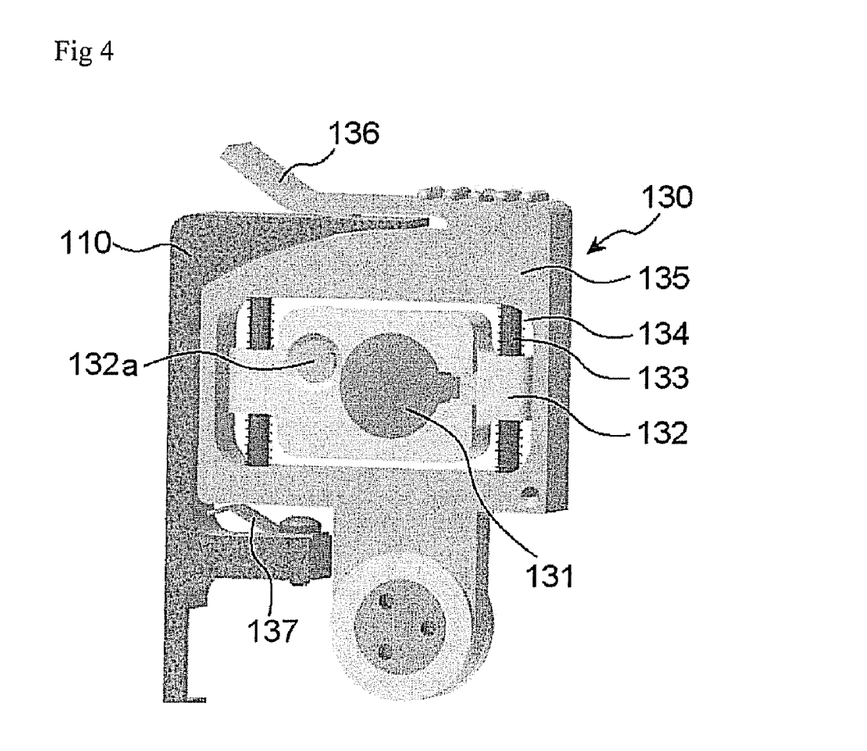
FIG. 4 is a perspective view illustrating an exemplary embodiment of a structure of a vibrator according to the present invention.

FIG. 4 is a perspective view showing an exemplary embodiment of a configuration of the vibrator according to the present invention.

As illustrated in FIG. 4, the vibrator 130 includes a vibration motor 131 disposed on a lower side of the vibrator 130 on a side opposite to the chip 120, a holder 132 that incorporates the vibration motor 131 therein and serves to fix the chip 120 on an upper side of the vibrator 130 to transfer vibrations thereto, a shaft 133 connecting the holder 132 to a external frame 135 so that the holder 132 is movable along therewith and a restrictive member 134, such as a spring, inserted into the exterior of the shaft 133 to elastically restrict the movement of the holder 132.

The vibration motor 131 as oriented in FIG. 4 vibrates vertically relative to a laser irradiation direction. A vibration force of the vibration motor 131 is elastically restricted by the spring 134 inserted into the shaft 133, thereby making the chip 120 disposed at the upper portion (or side) of the vibration motor 131 subjected to linear reciprocating motion in an axial direction of the shaft 133. A vibration amplitude is determined depending on an operating voltage of the vibration motor 131 and a spring constant of the spring 134.

A chip discharge part 132a, such as a discharge pin, is inserted and installed at one side of the holder 132 in a direction perpendicular to the upper and lower sides of the vibrator 130. The chip discharge pin 132a is utilized to efficiently remove the chip 120 installed at the upper portion of the holder 132 after the reaction is completed. In an exemplary embodiment, the chip discharge pin 132a may be movable or protrude at an end opposite to the one side (e.g. proximate an inner portion of the chip) while being pressurized by a user's finger at the one side of the holder 132 in order to separate the holder 132 and the chip 120 from each other.

As in the illustrated exemplary embodiment, the laser is irradiated on the surface of the chip 120 substantially perpendicular to the axial direction of the shaft 133 and substantially widely and evenly irradiated to the sample introduced in the reaction chamber 121a by the reciprocating motion of the chip 120. Advantageously, the vibrations transferred to the chip 120 efficiently function to mix the sample and magnetic beads within the reaction chamber 121a and at the same time move cells unexposed to the laser to a center of an irradiation area of the laser generator 140. The reaction chamber 121a has a reaction area larger (or wider) than the irradiation area supplied by the laser generator 140 to accommodate the reciprocating motion of the chip 120.

In an exemplary embodiment, the vibrator 130 may be pivotally connected to the main body 110 such that it can be rotatively opened from the main body 110 for replacement of the chip 120 (see FIGS. 1A and 1B). During the cell lysis procedure, the vibrator 130 is closed and is fixedly connected to the main body 110 through fixing member, such as a hook 136 and/or a plate spring 137 as illustrated in FIG. 4. The fixing member reduces or effectively prevents the vibrator 130 from randomly opening by vibrations during laser irradiation. In an alternative embodiment, such opening and closing procedure of the vibrator 130 may be automatically conducted by using an internal driving means.

Figure 5:
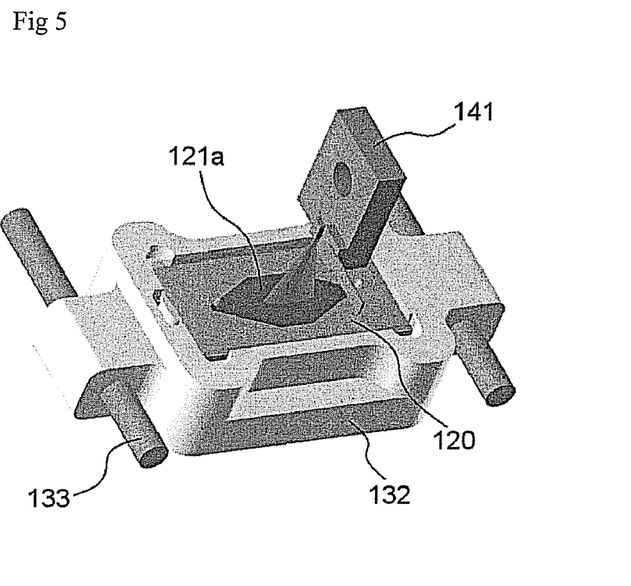
FIG. 5 is a perspective view illustrating an exemplary embodiment of a laser being irradiated to a cell lysis chip according to the present invention.
Figure 6:
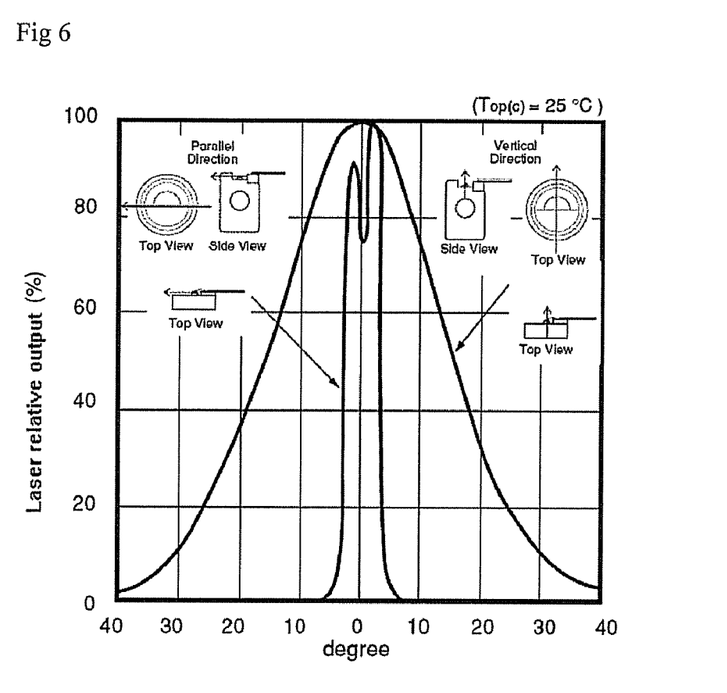
FIG. 6 is a graph illustrating an exemplary embodiment of a directionality of the laser supplied by a laser diode according to the present invention as an irradiation angle (degree) in terms of a laser output power (percentage %)
Figure 7:
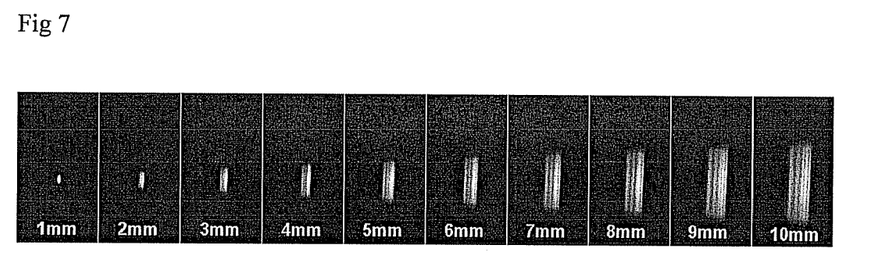
FIG. 7 is a photograph illustrating an exemplary embodiment of a beam profile in terms of a laser irradiation distance relating to FIG. 6.

FIG. 5 is a perspective view showing an exemplary embodiment of a laser being irradiated to a cell lysis chip according to the present invention, FIG. 6 is a graph presenting an exemplary embodiment of a directionality of a laser supplied by a laser diode according to the present invention as an irradiation angle in terms of a laser output power, and FIG. 7 is a photograph showing a beam profile in terms of a laser irradiation distance relating to FIG. 6.

In an exemplary embodiment, in order to transfer sufficient energy to disrupt cells, a laser power is 100 milliwatts (mW) or more for a continuous wave ("CW") laser and 3 millijoules per pulse (mJ/pulse) or more for a pulse laser. To implement a small-sized cell lysis apparatus that is capable of satisfying the above requirement and including a battery, in one exemplary embodiment, the laser diode 141 has about 1 W grade of the laser power.

As illustrated in FIG. 5, the laser diode 141 irradiates a laser to the cell lysis chip 120 installed at the upper portion of the holder 132 at a prescribed distance, thereby transferring light energy having sufficient power to disrupt cells or viruses thereto. In an exemplary embodiment, the laser irradiated by the laser diode 141 has different irradiation angles with respect to both axes. In this way, a maximum area is secured where the laser irradiates to the reaction chamber 121a, such as where the reaction chamber 121a is of a channel form.

An exemplary embodiment of irradiation characteristics of the laser diode 141 suitable for transferring sufficient energy to disrupt cells is illustrated by the directionality graph of FIG. 6. In the laser power based on FWHM (Full Width at Half Maximum), the laser is irradiated at the angle of 8° in a horizontal direction and at the angle of 32° in a vertical direction.

In the laser power based on FWHM, a relative comparison of the irradiation area in terms of the actual irradiation distance of the laser diode 141 can be found in the beam profile of FIG. 7. According to the beam profile, the irradiation area at the irradiation distance of 6 millimeters (mm) adopted as an experimental value is 2.89 $mm^2$, and where the cell lysis chip 120 provided with the reaction chamber 121a having a width of 15 $mm^2$, it is possible to secure the direct irradiation area of about 19%.

When the moving distance of the chip 120 is adjusted to ±0.8 mm by vibrating the holder 132 based on the above-described principle, the laser irradiation area covers about 56% of the reaction chamber 120 having the width of 15 $mm^2$, thereby enlarging the irradiation area about three (3) times compared to the case of having no vibration.

Figure 8:
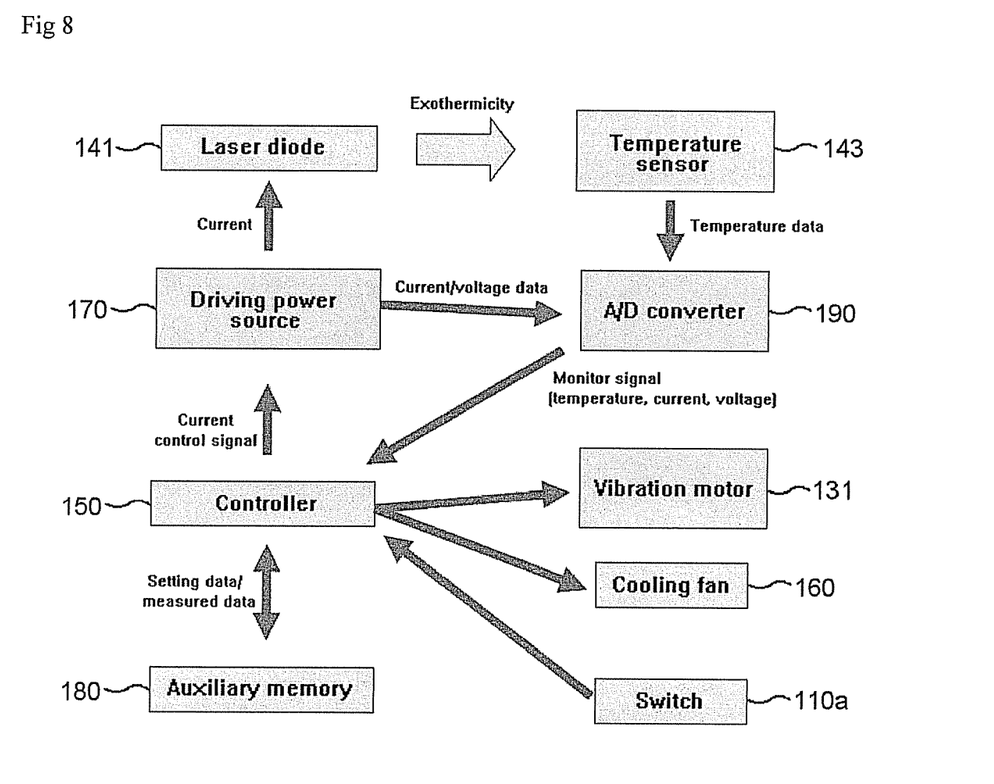
FIG. 8 is a block diagram illustrating an exemplary embodiment of an operation of the apparatus for disrupting cells or viruses using a laser and magnetic beads according to the present invention.

Hereinafter, an exemplary embodiment of an operation of the apparatus for disrupting cells or viruses using a laser and magnetic beads according to the present invention will be described in detail with reference to a block diagram of FIG. 8.

The controller 150 may include a software program to operate the laser diode 141, the vibration motor 131 and the cooling fan 160 for a designated time period through a certain input means and executes the program by an action of the switch 110a. In an exemplary embodiment the controller 150 may include a separate timer (not shown).

The controller 150 transmits a current control signal to the driving power source 170 to supply a corresponding current, thereby allowing a predetermined amount of laser to be irradiated by the laser diode 141. The heat sink 142 absorbs and disperses the heat generated by laser irradiation in order to distribute and reduce concentrations of the heat. The temperature sensor 143 installed at one side of the heat sink 142 (see FIG. 2) measures the temperature raised by exothermic reaction and temperature calibration data is converted into a corresponding digital signal by an A/D converter 190. The temperature data is transmitted to the controller 150.

At the same time, a current value flowing in the laser diode 141 and a voltage value therein are converted into digital signals through the A/D converter 190 and transmitted to the controller 150.

The controller 150 compares the current and voltage values of the laser diode 141 inputted as monitor signal with initial setting values to control the laser diode 141 to maintain a constant irradiation amount for a designated time period. Approximately simultaneously, the controller 150 operates the cooling fan 160 depending on the inputted temperature data and emergently controls the level of laser irradiation when the temperature data exceeds a preset threshold temperature. Further, the controller 150 controls the operation and amplitude of the vibration motor 131 on the basis of setting data.

The controller 150 is provided with a separate auxiliary memory 180 that stores and maintains the setting and calibration data even when the power is turned off. In exemplary embodiments, the auxiliary memory 180 may be—EEPROM (Electrically Erasable Programmable Read Only Memory) which is programmable, is only readable and can be erased by an electric signal in view of cost reduction and convenience, UVEPROM (Ultra Violet Erasable PROM), flash memory or the like.

In an exemplary embodiment, various types of parameter data required for the operation of the apparatus 100 are inputted, such as by a computer (not shown), via a wire and/or a wireless communication network and stored in the auxiliary memory 180, such as EEPROM, to be also maintained in the state of power-off, thereby rendering the independent operation of the apparatus 100 possible even after the connection to the computer is cut off.

The operation of the cooling fan 160 may be controlled based on the temperature calibration data of the heat sink 142 as set forth above, but in an alternative embodiment, it is also possible to drive the cooling fan 160 all the time by switching through a random modification of the operation condition or to drive it only when the laser is irradiated.

As in the illustrated exemplary embodiments, the apparatus for disrupting cells or viruses using a laser and magnetic beads may be miniaturized by using an inexpensive, small-sized, high power laser diode and also may be implemented as an independent system that is operable by only a battery, thereby making it easily transportable and handy to carry.

In the illustrated exemplary embodiments, since the apparatus of the present invention has a holder structure that allows the cell lysis chip to be vibrated vertically relative to a laser irradiation direction, it can secure a wider laser irradiation area and also improve cell lysis efficiency by employing only a low power laser, without using any other diffusion lens.

In the illustrated exemplary embodiments, the apparatus vibrates the laser and magnetic beads together, thereby disrupting cells or viruses more rapidly and efficiently.

Now, the present invention will be described in detail with reference to the following examples, which are not intended to limit the scope of the present invention.

Experimental Example 1

Cell Lysis Efficiency of Laser Irradiation

In order to estimate cell lysis efficiency of the apparatus 100 for disrupting cells or viruses using a laser and magnetic beads according to the present invention, Gram-negative bacteria, *E. coli* cells were divided into four groups based on its concentrations ($2\times10^4$, $2\times10^3$, $2\times10^2$ and $2\times10$ cells/µl) and subjected to PCR analysis. At this time, cell lysis was conducted at the following conditions: 0.8 W of a laser power, 40 seconds of a laser irradiation time and 6 mm of a laser irradiation distance. The magnetic beads were introduced into a reaction chamber at the concentration of $10^7$ beads/µl and the size thereof was 1 µm. Among controls, a negative control refers to a case where PCR was performed by using only a supernatant that was obtained by centrifuging the *E. coli* cell culture solution at 13,200 rpm for 5 minutes. Further, a positive control (Boiling) refers to a case where PCR was performed on DNA released after boiling *E. coli* cells at 95° C. for 5 minutes.

Figure 9:
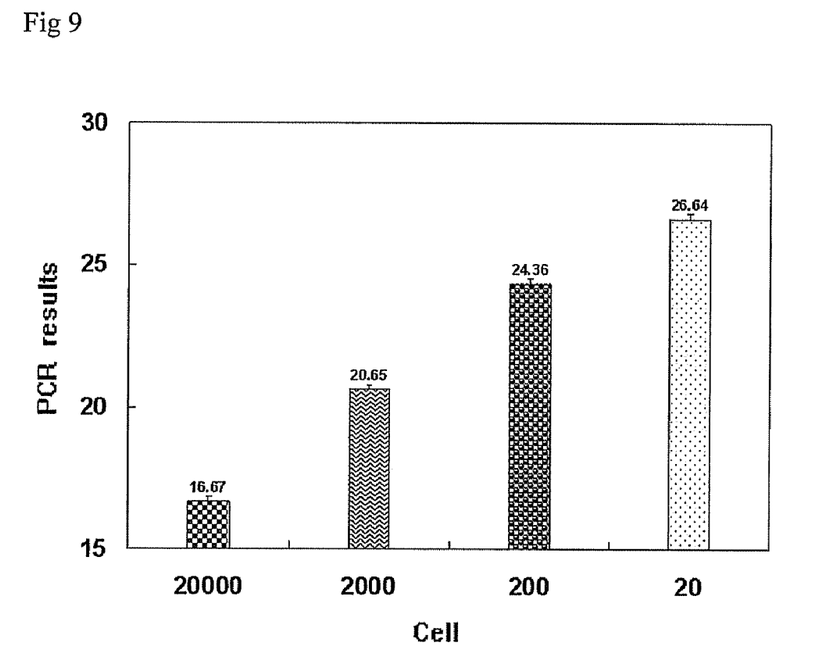
FIG. 9 is a graph illustrating PCR results of DNA released from *E. coli* cells with respect to DNA concentration, wherein the cells are irradiated with a laser in the presence of magnetic beads.
Figure 10:
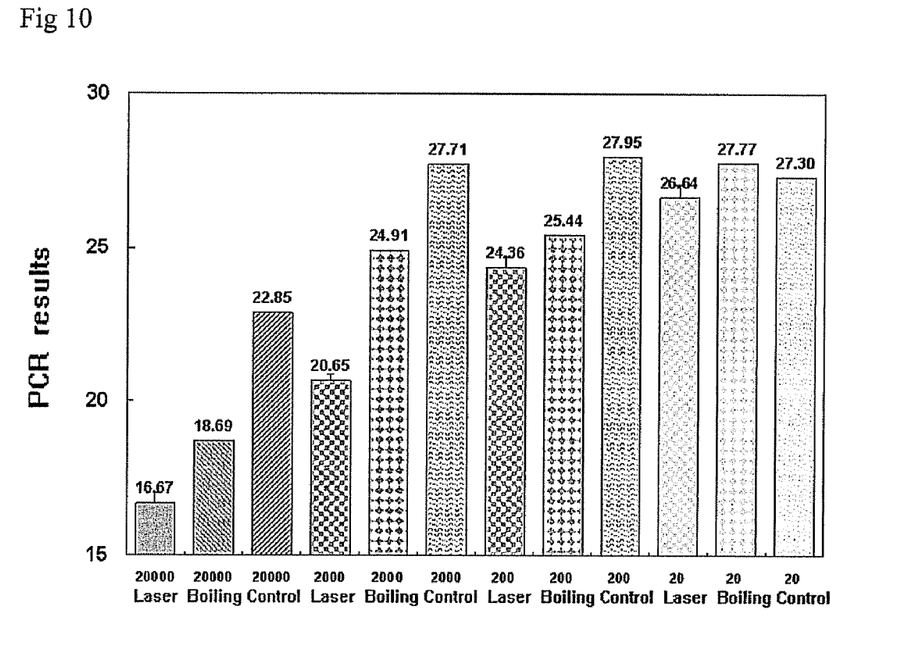
FIG. 10 is a graph relatively comparing the PCR results described in FIG. 9 with those of negative and positive (Boiling) controls.

FIG. 9 is a graph illustrating PCR results of DNA released from *E. coli* cells with respect to DNA concentration, wherein the cells are irradiated with a laser in the presence of magnetic beads, and FIG. 10 is a graph relatively comparing the PCR results described in FIG. 9 with those of the negative and positive (Boiling) controls. The bars represent the cross point ("Cp") value of the concentration of the amplified DNA, and the error bars indicate a standard deviation when three replicates were conducted with respect to each condition.

Referring to FIGS. 9 and 10, it was found that the cell lysis efficiency of the apparatus 100 using a laser is constantly increased in proportion to the concentration of the amplified DNA and is significantly higher than those of the negative and positive controls at any concentration condition. Therefore, it can be seen that the apparatus 100 of the present invention can efficiently disrupt various cells including Gram-negative bacteria regardless of the cell concentration in spite of using the low laser power (0.8 W).

Experimental Example 2

Cell Viability after Laser Irradiation

In order to examine cell viability after laser irradiation by using the apparatus 100 for disrupting cells or viruses using a laser and magnetic beads according to the present invention, Gram-negative bacteria, *E. coli* cells were irradiated with a laser in the presence or absence of magnetic beads to occur cell lysis, cultured on a Petrifilm (manufactured by 3M, *E. coli*/Coliform Count plate) for 12 hours or more, and subjected to colony counting. At this time, the concentration of the cell culture solution was $10^5$ cells/µl. Further, cell lysis was conducted at the following conditions: 1.0 W or less of a laser power, 40 seconds of a laser irradiation time and 6 mm of a laser irradiation distance. The magnetic beads were introduced into the reaction chamber at the concentration of $10^7$ beads/µl and the size thereof was 1 µm.

Figure 11:
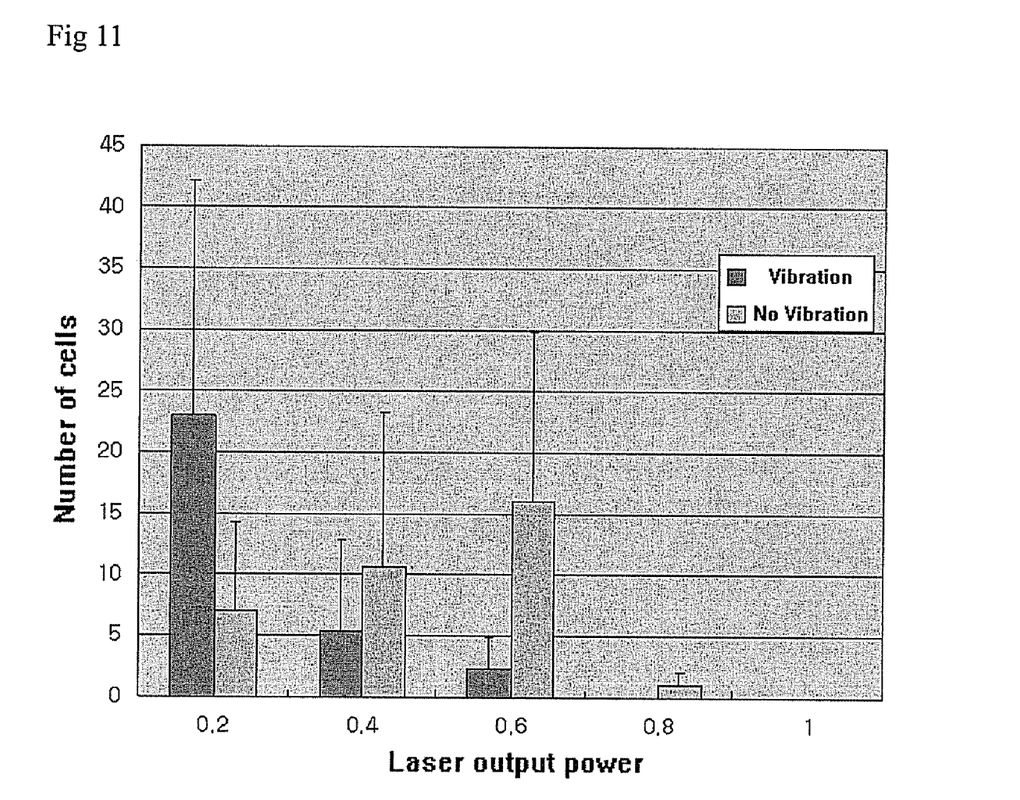
FIG. 11 is a graph illustrating the results of colony counting after the cells are irradiated with a laser in the presence of magnetic beads compared with those when irradiating a laser only.

FIG. 11 is a graph presenting the results of colony counting after the cells are irradiated with a laser in the presence of magnetic beads in comparison with those when irradiating only a laser. The vibration bar represents a state that the vibration motor is operated and the error bars indicate a standard deviation when three replicates were conducted with respect to each condition.

As illustrated in FIG. 11, when the chip 120 was vibrated with an increased laser power at the level of 0.4 W or more, the number of cell colony was sharply decreased. That is, the use of the vibration motor 131 can efficiently and rapidly disrupt cells at the lower laser power compared with the case of irradiating only a laser.

While the present invention has been particularly shown and described with reference to exemplary embodiments thereof, it will be understood by those of ordinary skill in the art that various changes and modifications may be made in the form and details of the described embodiments without departing from the spirit and scope of the invention as defined by the appended claims.

What is claimed is:

1. An apparatus for disrupting cells or viruses using a laser and magnetic beads, comprising:
   a cell lysis chip including a reaction chamber including a solution of a sample containing the cells or viruses and the magnetic beads;
   a vibrator reciprocating in a first direction, the cell lysis chip disposed in the vibrator, and the vibrator reciprocating the cell lysis chip including the reaction chamber, in the first direction;
   a laser generator disposed facing the vibrator, and irradiating the laser to the solution in the reaction chamber of the cell lysis chip reciprocating in the first direction; and
   a controller controlling operations of the vibrator and the laser generator.

2. The apparatus for disrupting cells or viruses according to claim 1, wherein the vibrator comprises:
   a vibration motor vibrating in the first direction;
   a holder including the vibration motor therein and being reciprocated in the first direction with the vibrating of the vibration motor, the cell lysis chip disposed in the holder and reciprocating in the first direction along with the reaction chamber;
   a shaft connecting the holder to an external frame of the vibrator, such that the holder including the cell lysis chip disposed therein is movable in the first direction along the shaft and relative to the external frame, and the cell lysis chip including the reaction chamber is reciprocated in the first direction; and
   a restrictive member disposed on the exterior of the shaft and elastically restricting the movement of the holder along the shaft relative to the external frame.

3. The apparatus for disrupting cells or viruses according to claim 2, wherein the restrictive member is a spring.

4. The apparatus for disrupting cells or viruses according to claim 2, wherein the first direction in which the vibration motor vibrates is perpendicular to an irradiation direction of the laser from the laser generator.

5. The apparatus for disrupting cells or viruses according to claim 1, wherein the laser generator comprises a laser diode ("LD").

6. The apparatus for disrupting cells or viruses according to claim 5, wherein the laser supplied by the laser diode has different vertical- and horizontal-irradiation angles.

7. The apparatus for disrupting cells or viruses according to claim 1, wherein the laser generator comprises a heat sink absorbing heat generated by laser irradiation and dispersing the heat.

8. The apparatus for disrupting cells or viruses according to claim 1, wherein the laser generator comprises a temperature sensor detecting temperature calibration date of a temperature raised by laser irradiation, the laser generator transmitting the detected temperature calibration data to the controller.

9. The apparatus for disrupting cells or viruses according to claim 1, wherein the laser generator comprises a cooling fan installed at one side of the laser generator, operated by the controller and lowering a temperature from heat generated within the apparatus by air.

10. The apparatus for disrupting cells or viruses according to claim 1, wherein the cell lysis chip comprises:
    a chip body including the reaction chamber formed at a center of the chip body and an opened top surface where the reaction chamber is formed; and
    a chip cover attached to the top surface of the chip body, overlapping an upper portion of the reaction chamber including the opened top surface, and allowing the laser to pass through the chip cover and to the solution in the reaction chamber, the chip cover including a sample inlet hole and a sample outlet hole formed to be penetrated towards the reaction chamber.

11. The apparatus for disrupting cells or viruses according to claim 10, wherein the reaction chamber has a reaction area wider than a laser irradiation area supplied by the laser generator.

12. The apparatus for disrupting cells or viruses according to claim 2, wherein the laser generator comprises a laser diode as a light source and the controller comprises a timer such that the laser diode and the vibration motor are driven for a designated time period.

13. The apparatus for disrupting cells or viruses according to claim 1, further comprising an auxiliary memory storing parameter data required for operation of the laser and transmitting the parameter data to the controller.

14. The apparatus for disrupting cells or viruses according to claim 13, wherein the auxiliary memory is one of EEPROM (Electrically Erasable Programmable Read Only Memory), UVEPROM (Ultra Violet Erasable PROM), flash memory, and a combination including at least one of the foregoing.

15. The apparatus for disrupting cells or viruses according to claim 1, further comprising a driving power source of the vibrator and the laser generator, the driving power source being a battery.

* * * * *